US012788933B2

(12) United States Patent
Rosano García

(10) Patent No.: US 12,788,933 B2
(45) Date of Patent: Nov. 10, 2026

(54) ASSISTED BREATHING APPARATUS AND METHOD

(71) Applicant: IQUANTUM PATENT FACTORY S.A. DE C.V., Mexico City (MX)

(72) Inventor: Julio Alberto Rosano García, San Pedro Cholula (MX)

(73) Assignee: IQUANTUM PATENT FACTORY S.A. DE C.V., Mexico City (MX)

( * ) Notice: Subject to any disclaimer, the term of this patent is extended or adjusted under 35 U.S.C. 154(b) by 692 days.

(21) Appl. No.: 18/021,608

(22) PCT Filed: Aug. 19, 2021

(86) PCT No.: PCT/MX2021/050047
§ 371 (c)(1),
(2) Date: Feb. 16, 2023

(87) PCT Pub. No.: WO2022/039586
PCT Pub. Date: Feb. 24, 2022

(65) Prior Publication Data

US 2023/0321388 A1 Oct. 12, 2023

(30) Foreign Application Priority Data

Aug. 19, 2020 (MX) .................... MX/a/2020/008822

(51) Int. Cl.
*A61M 16/20* (2006.01)
*A61M 16/00* (2006.01)
(Continued)

(52) U.S. Cl.
CPC ...... *A61M 16/204* (2014.02); *A61M 16/0051* (2013.01); *A61M 16/085* (2014.02);
(Continued)

(58) Field of Classification Search
CPC ................ A61M 16/009; A61M 16/12; A61M 2016/103; A61M 16/122; A61M 16/125; A61M 16/205
See application file for complete search history.

(56) References Cited

U.S. PATENT DOCUMENTS 5,097,424 A 3/1992 Ginevri et al.
5,161,525 A 11/1992 Kimm et al.
(Continued)

FOREIGN PATENT DOCUMENTS

WO WO-2021231363 A1 * 11/2021 ............ A61M 16/12

OTHER PUBLICATIONS

International Search Report issued in connection with the corresponding International Application No. PCT/MX2021/050047 on Dec. 14, 2021.

*Primary Examiner* — Joseph D. Boecker
*Assistant Examiner* — Jaeick Jang
(74) *Attorney, Agent, or Firm* — Defillo & Associates, Inc.; Evelyn A. Defillo

(57) ABSTRACT

The present invention refers to a respiratory assistance device that provides respiratory support to patients when they are unable to do it on their own or have difficulties in doing so, where it is made up of a series of electronic, mechanical and control arrangements to execute such actions, providing a constant flow of air/oxygen to the patient.

20 Claims, 11 Drawing Sheets

(51) Int. Cl.
*A61M 16/08* (2006.01)
*A61M 16/12* (2006.01)
*A61M 16/16* (2006.01)

(52) U.S. Cl.
CPC .......... *A61M 16/125* (2014.02); *A61M 16/16* (2013.01); *A61M 16/205* (2014.02); *A61M 2016/0027* (2013.01); *A61M 2202/0208* (2013.01); *A61M 2205/3584* (2013.01); *A61M 2230/432* (2013.01)

(56) References Cited

U.S. PATENT DOCUMENTS

| | | | | |
|---|---|---|---|---|
| 10,668,239 | B2 | 6/2020 | Kimm et al. | |
| 11,559,643 | B2 | 1/2023 | Sanborn | |
| 2013/0152923 | A1 * | 6/2013 | Andrieux .......... | A61M 16/0465 128/202.22 |
| 2014/0254305 | A1 | 9/2014 | Caso et al. | |
| 2016/0287824 | A1 | 10/2016 | Chang | |
| 2017/0128692 | A1 * | 5/2017 | Christopher ........... | A61B 5/097 |

* cited by examiner

ASSISTED BREATHING APPARATUS AND METHOD

TECHNICAL FIELD

The present invention belongs to the technical field of human needs, specifically, to the field of health; and medical sciences, more specifically to devices for introducing or administering gases into a human body, in an even more specific aspect to devices for influencing the respiratory system of patients by gas treatment by stimulating respiratory movement by mechanical means, pneumatic, electric and even more specifically, the present invention relates to an assisted breathing apparatus and method.

BACKGROUND OF THE INVENTION

There are currently disclosed, in the state of the art, a series of devices, utensils and apparatus that are aimed at providing a means of assisting the breathing of a patient with breathing difficulties, it is therefore that these devices, also called ventilators, refer generally to mechanical fans that incorporate a generally low inertia, variable speed airflow thrust means that are specifically tailored to provide the full functionality of the fan; the prior art includes a wide variety of mechanical ventilators for patients requiring respiratory support.

Unfortunately, such mechanical ventilators have traditionally been configured as relatively large devices occupying a relatively large volume of the limited space available in operating rooms and patient recovery rooms. Furthermore, such prior art mechanical fans are typically low in efficiency such that relatively large amounts of power are required to operate the device. Furthermore, prior art mechanical ventilators have not been truly portable devices in the sense that such devices have a relatively large weight and bulk that limit their portability.

Furthermore, in general, mechanical ventilators have achieved improved functionality with respect to their ability to deliver a variety of modes of respiration to the patient through the use of rotary drive compressors that operate at low pressure to deliver the breath to the patient. Such drag compressors can operate in variable speed or constant speed mode.

Mechanical ventilators operating in variable speed mode provide inspiratory support (i.e., inhalation assist) to a patient by rapidly accelerating the compressor from a standstill followed by rapid deceleration during the expiratory (i.e., exhalation) phase of the breathing cycle. breathing Unfortunately, such rapid acceleration and deceleration require complex drive circuitry for the compressor and the consumption of high electrical currents. The current draw is relatively high for such variable speed drive compressors, which adds to the overall cost of the mechanical fan. In addition, the high current requirement requires the addition of bulky and heavy batteries to provide backup battery power for emergency backup when the ventilator is not connected to a stationary power source.

Alternatively, rotary drag compressors can be run in constant speed mode to remove the limitations imposed by the high current requirements of variable speed compressors. Unfortunately, such constant speed drive compressors have their own set of inherent shortcomings that detract from the overall usefulness of the mechanical ventilator. For example, because the compressor runs at a constant speed, power is continuously consumed even during the expiratory phase (ii, exhalation) when no air or gas is supplied to the patient. Although power consumption can be reduced by recirculating the airflow during exhalation to a compressor inlet, a considerable amount of battery backup power is still required to operate the mechanical ventilator when not connected to a stationary power source.

As can be seen, there is a need in the art for a mechanical ventilator that is small in size and low in weight to improve its portability. In addition, there is a need in the art for a portable mechanical ventilator that can provide respiratory support to a patient for extended periods without the limitations of a stationary power source. In addition, there is a need in the art for a portable mechanical ventilator that provides respiratory support in volume and pressure control modes and that can be operated safely and quietly in the noise sensitive environments of operating rooms, intensive care units, intensive care and patient recovery rooms.

At present there is no device of this nature, which records all the information programmed and collected during its operation.

This information could be processed and available on the internet worldwide, to improve medical protocols and procedures.

It is also known that in the European patent EP 0324275 B1 a ventilation synchronizer is broadly described in which the rising edge of an impedance signal is detected to indicate the start of spontaneous inspiration and a gas supply is available through a ventilator that is synchronized by a ventilation synchronizer to a selected point during the spontaneously inspired time period. In addition, apnea conditions are detected to activate a backup system to deliver gas to the patient periodically despite the lack of spontaneous breathing, and if desired, ventilator triggering and weaning need not be timed to be simultaneous with start of inspiration and exhalation; instead, this can be accomplished at selected times after the start of inhalation or exhalation. Ventilator activation and deactivation can also be accomplished in a manner that minimizes the effects of a wandering baseline. Instead of using the electrical impedance between two points on a person's chest to indicate spontaneous breathing, other signals may also be used which may be, for example, electromyograms, signals indicating chest muscle contractions, signals from pneumatic devices that indicate the movement of the patient's abdomen and ultrasound signals that indicate the movement of the patient's diaphragm.

Another document belonging to the state of the art of the present invention is the portable mechanical ventilator with a drag compressor detailed in US patent application US20030230307A1, which describes a ventilation device and system that includes a rotary compressor, preferably a rotary compressor. drag, which, at the start of each phase of inspiratory ventilation, is accelerated to a rate sufficient to deliver the desired inspiratory gas flow, and is subsequently stopped or decelerated to a basal flow level to allow the phase of expiratory ventilation to occur. The ventilation device is small and light enough to be used in portable applications. The ventilation device is efficient enough to run for long periods of time on internal or external batteries. Also provided is an oxygen mixing apparatus that uses solenoid valves having specific orifice sizes to mix desired amounts of oxygen into the inspiratory gas flow. Also provided is an exhalation valve having an exhalation flow transducer that incorporates a radio frequency database to provide an auxiliary controller with specific calibration information for the exhalation flow transducer.

In the same sense, US patent U.S. Pat. No. 9,925,346B2 is known, which mentions ventilation systems and methods with unknown exhalation flow, where ventilation systems and methods are provided that allow the patient to activate or initiate the delivery of a breath. In addition, systems and methods are provided to activate ventilation when the exhalation flow is unknown or unreliable by the ventilator, in the same way a series of methods and devices to vary the backup rate of a ventilator are disclosed in the document U.S. Pat. No. 8,051,852B2 in wherein a ventilation device provides ventilatory support to a patient in a timed back-up mode when the patient's breath is not detected or a spontaneous mode when the patient's breath is detected. The time threshold governing the backup mode is chosen to deviate from the expected normal breath time for the patient to promote patient-initiated ventilation in the spontaneous mode but allow backup ventilation in the event of apnea. Automated adjustments to the time threshold during the timed mode are made from the less vigilant time threshold to a more vigilant threshold at or near the time of the patient's expected normal respiration. These adjustments can be made from a minimum to a maximum watchdog time setting or incrementally between them as a function of time in timed mode, which is preferably the number of delivered machine breaths.

Finally, the US patent application US20190143059A1 is known as the document closest to that of the present invention, which reveals systems and methods of patient ventilation, where a mechanical ventilator is provided that includes a dashboard screen that identifies the current ventilatory status. of a patient within a global or universal ventilatory mechanic's map. This dashboard screen dynamically updates with the patient's condition and shows trends in the patient's ventilation over time. The map identifies the regions of safe and unsafe instructions are suggested for the patient, and the ventilator can display informational text, activate audio and/or visual alarms, and transmit alarm communications in response to a determination that the patient is approaching or has entered an unsafe region.

The disadvantages found in the prior art occur mainly in that current respirators have an excessive number of elements that make up their assembly, which, in addition to increasing their downtime, promote maintenance measures that are complex for the personnel who operate and maintain them, in addition to increasing the risk of a component failing, not to mention that the weight and volume are increased by the arrangement of the components. Additionally, there is no respirator that reliably promotes a reading of the patient's parameters in portability situations. The foregoing results in notorious disadvantages for the user since it prevents him from having a reliable respirator that can be used in demanding conditions with mechanical and structural support robust enough to operate without complications; For these reasons, there is a need for a device that offers the possibility of providing a means of breathing for patients who require this derived from a respiratory disease and that can operate without complications both in the patient and in the equipment.

Likewise, the greater the number of sensors and solenoid valves of the prior art, the greater the time and resources that the microprocessor must use to communicate with its peripherals and this is the reason why the microprocessor can only process the behavior of each a few times per second. respiratory cycle. What causes the necessary corrections to the programmed values to be given progressively and not immediately, which delays said corrections in one or more respiratory cycles to reach the expected or preset values.

Therefore, the present invention has the task of presenting a device and method that solves the previously described drawbacks and offers significant advantages in its utility, since it is a respiratory assistance device with characteristics similar to those described in the aforementioned documents., with a series of components in its structure that allow an easy and simple operation of the same, with integrated circuits and functions for data processing, without neglecting at any given moment the safety of both the operability and the device.

Thanks to the fact that this respiratory assistance device comprises a minimum number of components and sensors, the processing of the sensed parameters sent to the microprocessor, allows its response to be immediate, since at an average rate of one evaluation every thousandth of a second, the response sent to a solenoid valve to correct the parameter, it will only take the mechanical time of said component to carry out the correction, and that movement takes a fraction of a second.

BRIEF DESCRIPTION OF THE INVENTION

It is therefore a main object of protection, a respiratory assistance device that has an inlet section made up of a normal air channel fed by an air compressor and an oxygen channel where an oxygen tank supplies this gas and where both connections are arranged in parallel and preferably horizontally, and where these fluid inlet channels have, in a first aspect, an air connector made up of a normal air inlet channel while the second channel has the inlet of oxygen integrated in the same way by an oxygen conductor that connects with an oxygen inlet nozzle, characterized in that the air inlet has a primary channel defined by a cylindrical conductor that has a preferably hexagonal-shaped connector where This is continuously connected to a pressure regulator and this in turn is connected to a first initial air tube. D, arranged horizontally and with a preferential length of at least two orders greater than the normal air inlet, guides the air until it is deposited in an On/Off air solenoid valve; while for the oxygen inlet there is a continuous oxygen inlet nozzle coupled with an initial oxygen tube at each of its ends with a threaded rib that eventually connects to the oxygen connector, the oxygen inlet nozzle and at the opposite end of this connection is fixed with an oxygen On/Off solenoid valve, where later the oxygen and air are mixed, said mixture is transferred to a pressure control solenoid valve that is connected with a humidifier so that the mixture is humid and with a higher temperature with respect to its admission, later it is sensed by a flow sensor and is deposited in the patient's lungs through an air and oxygen outlet, while for the gases from the patient, there is a CO2 outlet made up of a CO2 outlet solenoid valve that finally leads to this gas through a gas outlet tube it is to a PEEP valve, which also integrates an arrangement with a differential pressure sensor.

According to the object of the invention, a method of respiratory assistance comprises the steps of: receiving a flow of oxygen from an oxygen source through an oxygen inlet nozzle; receiving a flow of air from a compressed air source through an air inlet; regulate the flow of oxygen using an oxygen pressure regulator; regulate the air flow using an air pressure regulator; preset through a plurality of graphical user interfaces displayed by one user interface, values related to tidal volume, positive end-expiratory pressure, trigger pressure, fraction of inspired oxygen, respiratory rate, and inspiration ratio/expiration, according to the needs required by a patient; control the passage of the oxygen flow regulated by means of an oxygen On/Off solenoid valve; control the passage of the regulated air flow by means of an On/Off air solenoid valve; mix the oxygen and air provided by the On/Off oxygen and air solenoid valves; humidify and increase the temperature of the moisture air/oxygen mixture by means of a humidifier; Sensing the value related to the amount of liters of air per minute (volume) of the wet mix by means of a flow sensor; Sensing the value related to the pressure of the inspiration and expiration gases through the input/output differential pressure sensor; leading the moistened mixture at a previously determined pressure and volume, towards an air/oxygen outlet channel that leads towards the patient during the inspiration process; monitor the value of CO2 contained in the exhaled gases using an exhaled air quality sensor to establish.

DESCRIPTION OF THE INVENTION

Figure 1:
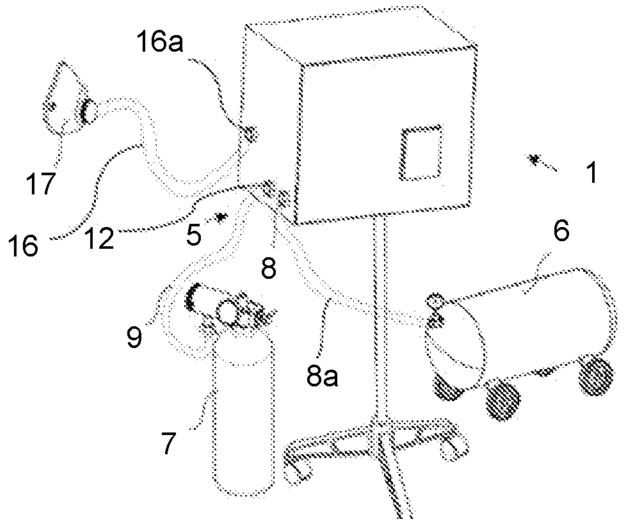
FIG. 1 shows an isometric view of the respiratory assistance apparatus (1) connected with an air compressor (6) and an oxygen tank (7), as well as an outlet with a mask (17).
Figure 2:
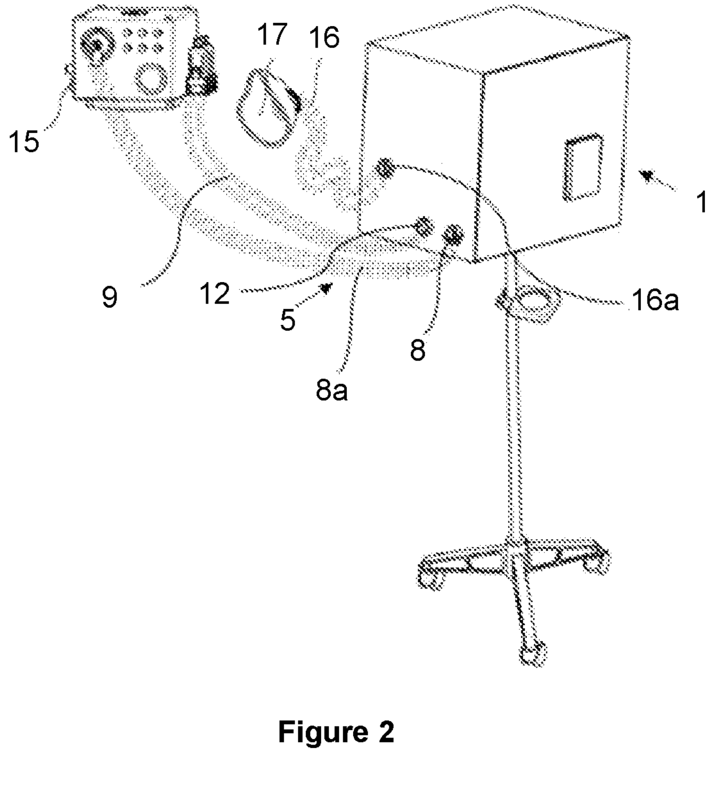
FIG. 2 shows an isometric view of the respiratory support apparatus connected to an air/oxygen supply arrangement and a mask (17).
Figure 3:
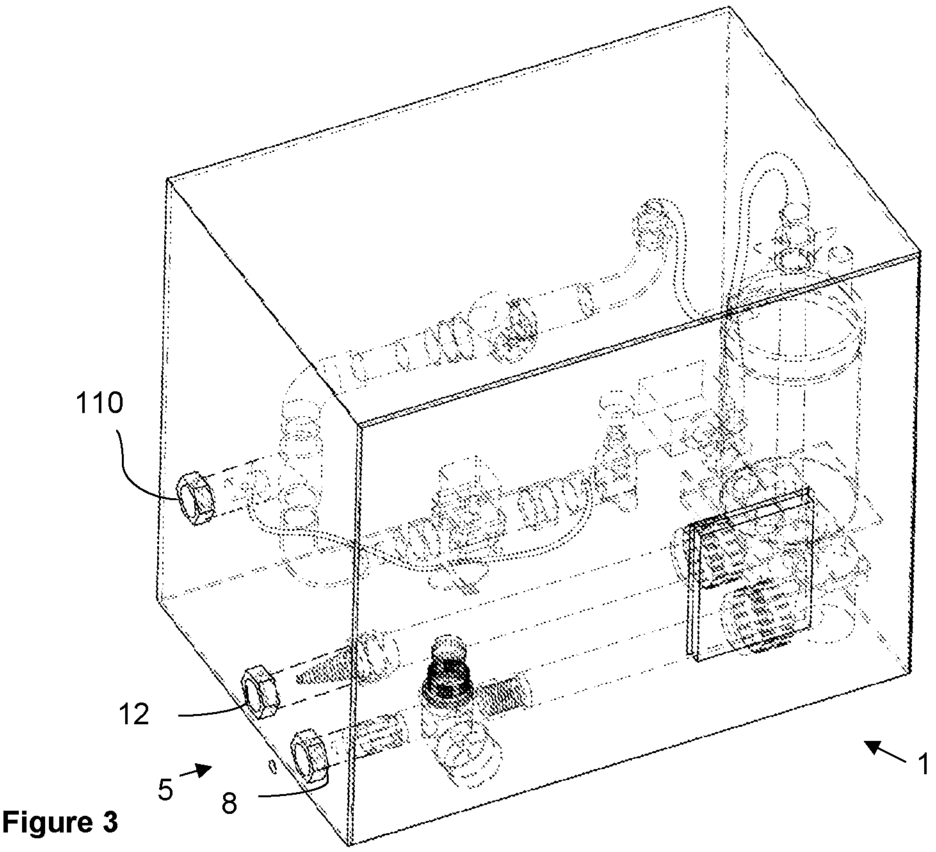
FIG. 3 shows an isometric view of the respiratory support apparatus (1).
Figure 4:
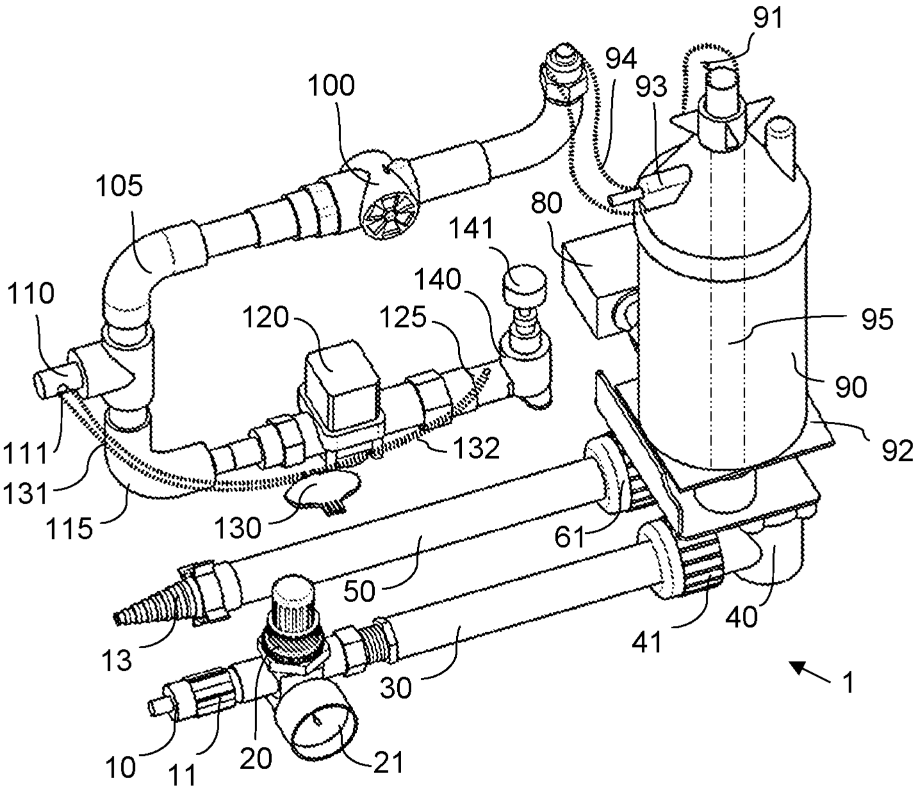
FIG. 4 shows an isometric view of the respiratory assistance apparatus (1).
Figure 5:
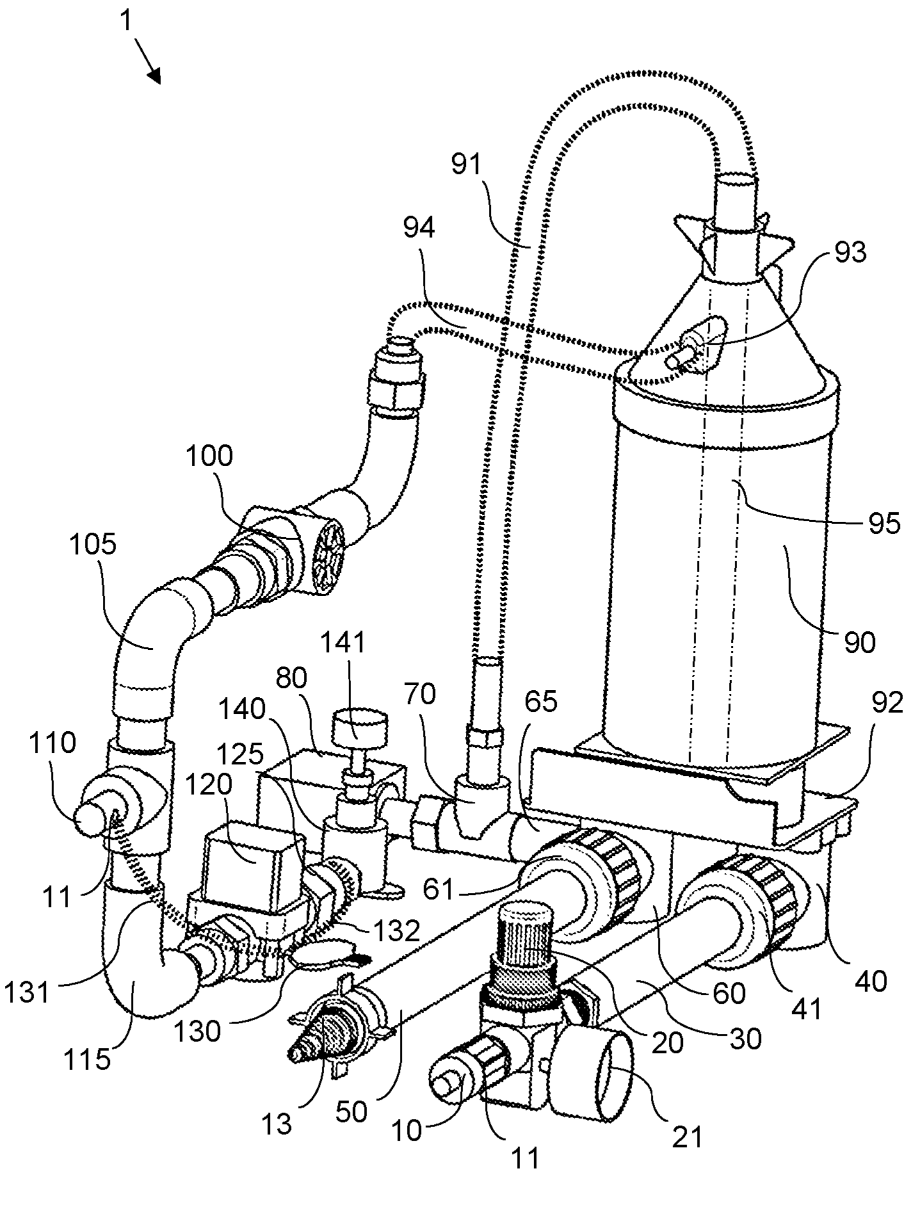
FIG. 5 shows an isometric view of the respiratory support apparatus (1).
Figure 6:
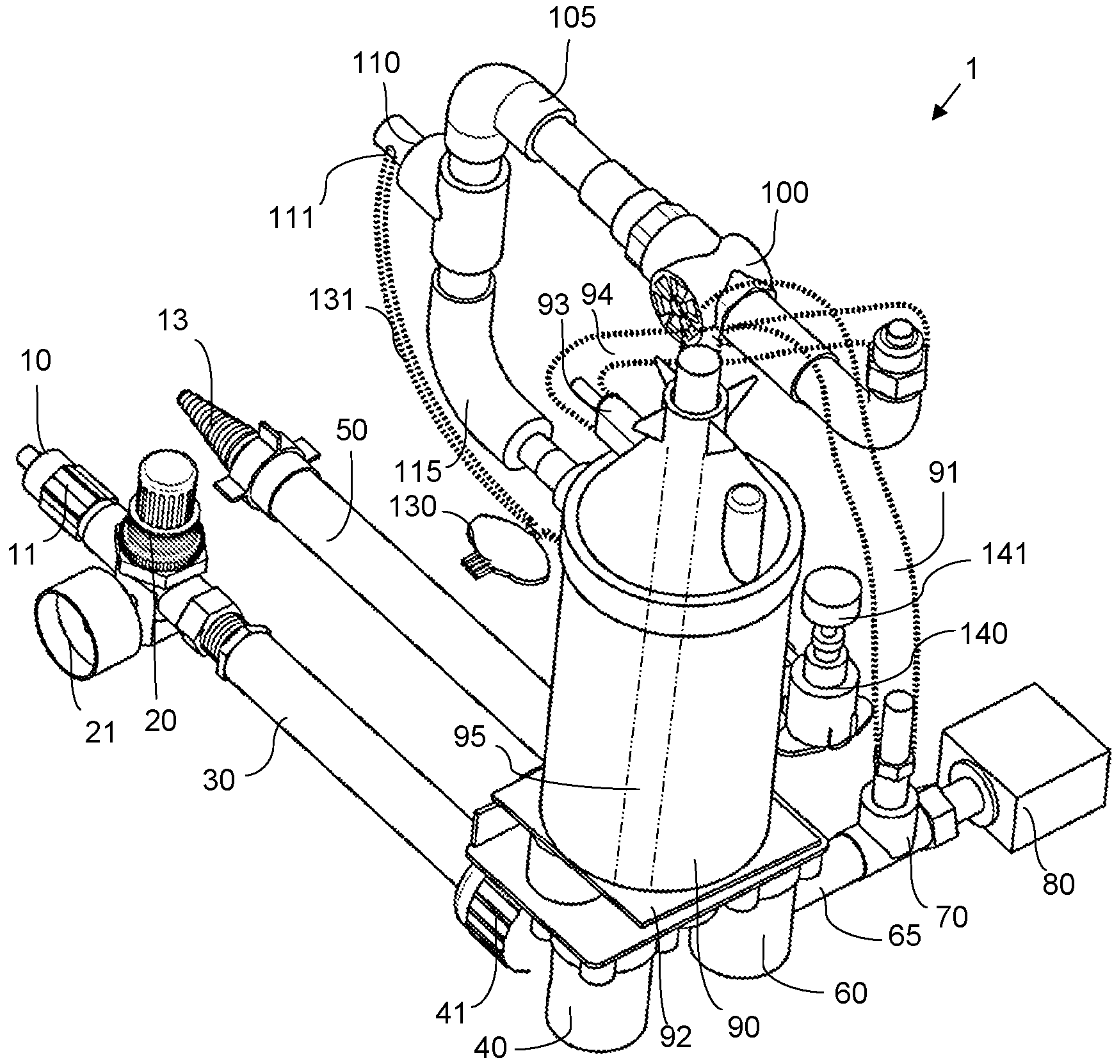
FIG. 6 shows an isometric view of the respiratory support apparatus (1).
Figure 7:
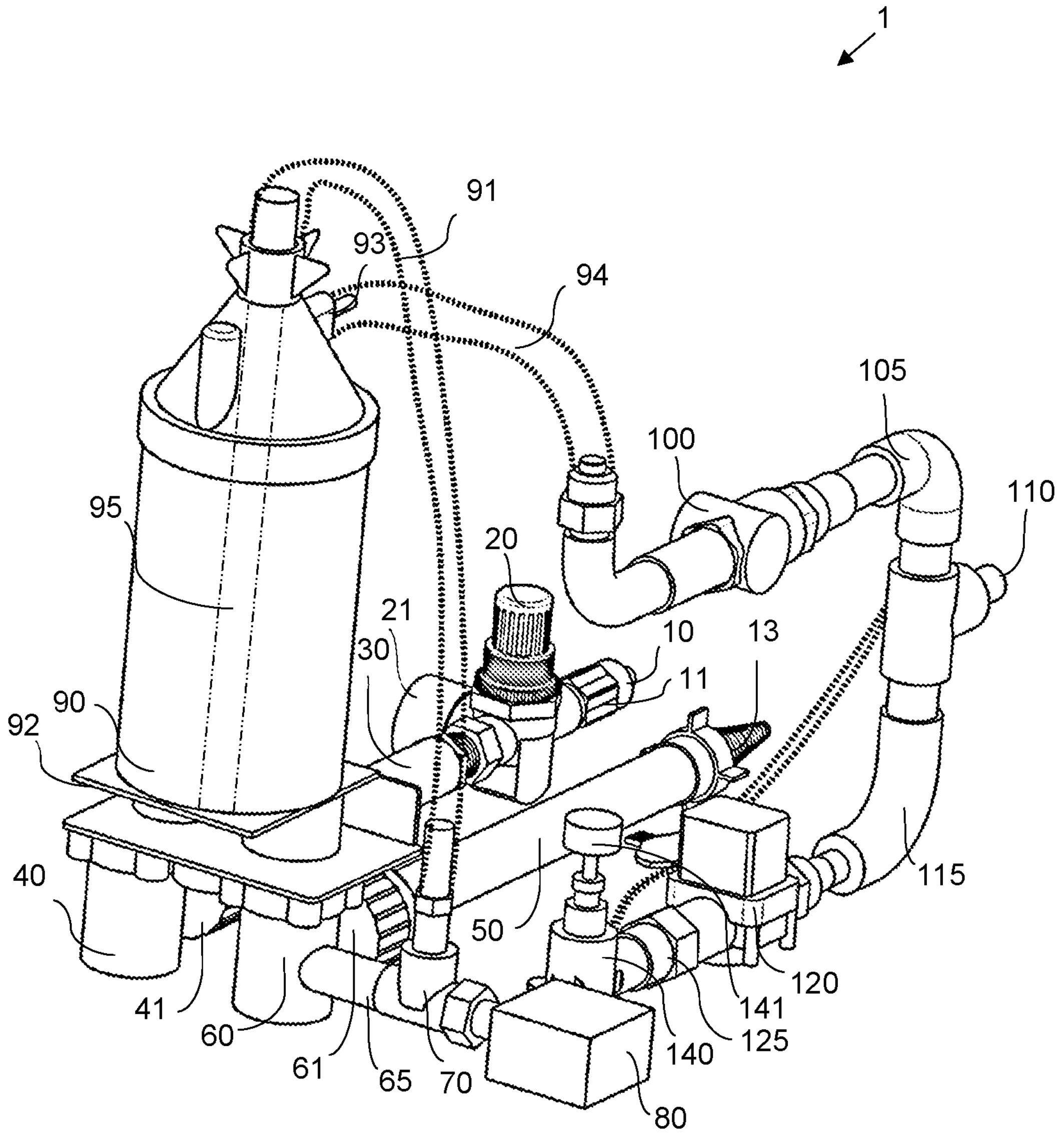
FIG. 7 shows an isometric view of the respiratory support apparatus (1).
Figure 8:
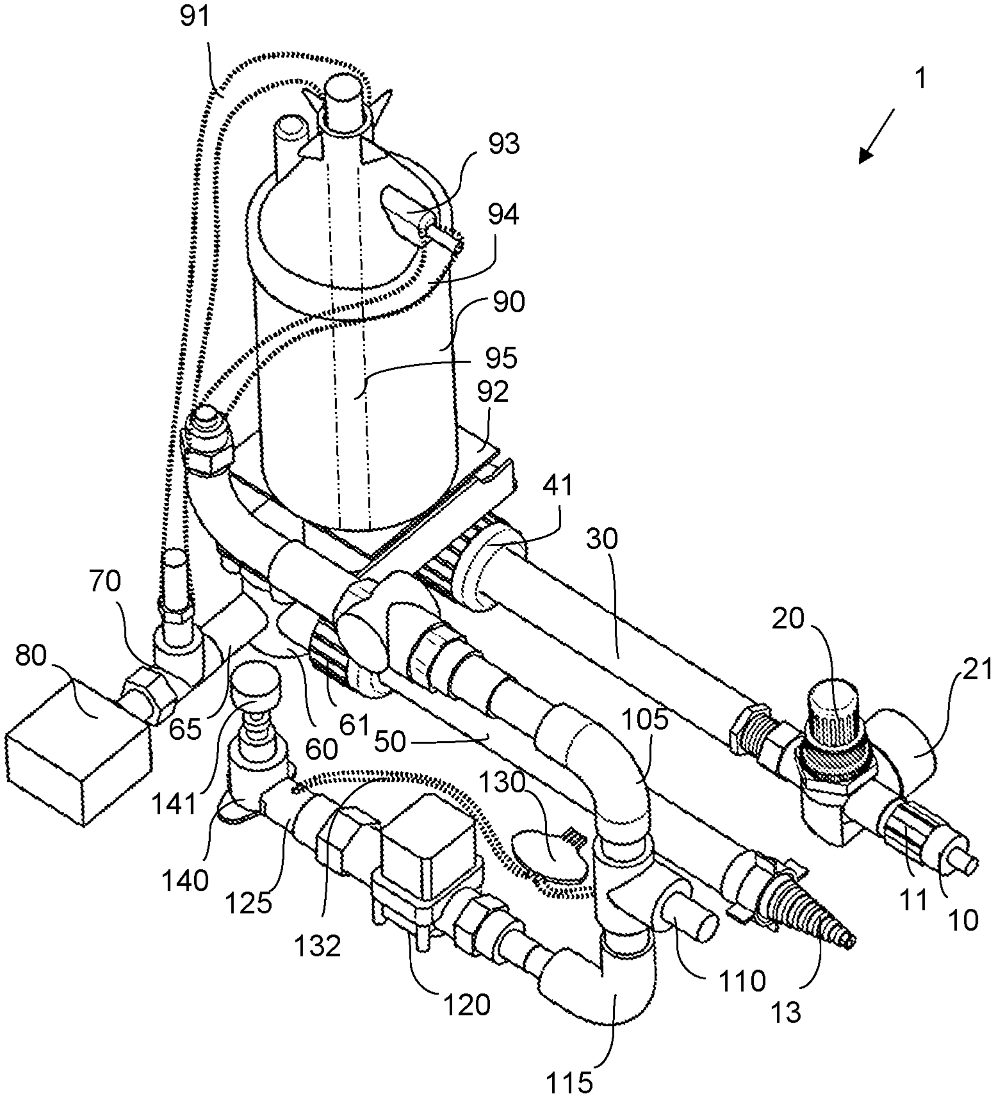
FIG. 8 shows an isometric view of the respiratory support apparatus (1).

In order to provide an understanding of the principles of the invention, reference will now be made to a preferred embodiment illustrated in the drawings, and specific language will be used to describe the same. However, it will be understood that no limitation on the scope of the invention is intended, such further alterations and modifications to the illustrated apparatus and such further applications of the principles of the invention as illustrated therein are contemplated as would normally occur now or in the future. future for a person skilled in the art to which the invention refers.

The present invention refers to a respiratory assistance device (1) that provides respiratory support to patients when they are unable to do it on their own or have difficulties in doing so, in general, having to configure and program the flow of breathing gases for the patient, only the patient's weight expressed in kilograms, the patient's height expressed in centimeters and the patient's gender (male or female) are required as input data. The apparatus object of the present invention provides an air/oxygen mixture so that it can be introduced into the patient's lungs, it is generally made up of a gas inlet section, a gas conduction section inside the apparatus, a portion for the admission of gases to the patient through a gas expulsion arrangement and a control and administration arrangement for the fluids contained inside the device, where it has a control card that includes a microcontroller which allows selecting the modes of operation of the device, being controlled from a user interface that displays a plurality of graphic selection interfaces where the personnel in charge of the operation of the equipment enters the values corresponding to the data required so that the air/oxygen flow from the device to the patient is the optimum.

Firstly, there is a respirator inlet section (5) which has a normal air channel (8*a*) fed by an air compressor (6), and an oxygen channel (9) where an oxygen tank (7) supplies this gas. Said air and oxygen channels (8*a*, 9) in turn, are coupled to the inlet section (5) by means of an air (8) and oxygen (12) connection, which are arranged in parallel and preferably horizontally.

Located at one of the ends of the respirator inlet section (5), the present invention also has an air/oxygen outlet channel (16) that is located attached to the respirator inlet section (5) by means of from an outlet connection (16*a*), where once the mixture has traveled through the interior of the device (1), it is expelled to be admitted to a patient through a mask (17) or an endotracheal tube (not shown).

In a second preferred embodiment of the invention, it has connections to the air/oxygen supplies (15) that are already found in medical units, therefore only the air (8*a*) and oxygen (9) channels are required.), coupled to their respective air (8) and oxygen (12) connections. In this mode, the air/oxygen outlet channel (16) is kept coupled with the respirator inlet section (5) by means of the connection (16*a*), and the free end of the channel (16) is enabled to couple the mask (17) or the endotracheal tube (not shown).

For the entry of normal air, there is a primary channel (10) defined by a preferably cylindrical conductor, emptied in its internal part and which has a connector (11) preferably hexagonal in shape where it is continuously connected with a pressure regulator (20) where it manages pressure values that are determined by the doctor or medical personnel in charge of programming the device and which in turn has a manometer (21) to display the pressure readings adjusted, where this pressure regulator is connected to a first initial air tube (30), arranged horizontally and with a preferential length of at least two orders greater than the normal air inlet (10) that conducts the air normal inside until it is deposited in an On/Off air solenoid valve (40), which for its coupling is assisted with an Air On/Off solenoid valve connection (41) that provides a hermetic seal by means of a mechanical that is adjusted by means of a thread present in the first initial air tube (30) and the solenoid valve (40).

While for the oxygen inlet there is a continuous oxygen inlet tube (50) from the oxygen connector (12) of an oxygen inlet nozzle (13), which at each of its ends has a threaded rib that eventually became Connected to the oxygen inlet nozzle (13) and at the opposite end of this connection, and through a connection with an oxygen On/Off solenoid valve (60), it is fixed with an oxygen On/Off solenoid valve (61). In one embodiment of the present invention, there is also a pressure regulator and a manometer (not shown in the figures) at the oxygen inlet (13) to regulate it like air, in the event that the source of oxygen supply lacks one.

Given that both the air On/Off solenoid valve (40) and the oxygen On/Off solenoid valve (60) are coupled together, an air/oxygen mixture is developed inside, where said mixture is sent to a humidifier (90) by means of a pressure control solenoid valve (70) that is coupled to an air/oxygen outlet (65), where said pressure control solenoid valve (70), in turn, is controlled by a servomotor (80), which in one embodiment of the invention uses a stepper motor, which regulates each respiratory cycle. As previously described, said pressure control solenoid valve (70) is a solenoid valve that is connected to the humidifier (90) by means of a connection means (91), where the humidifier (90) is integrated by a container cylindrical in shape, without being limited to this shape, which is arranged centrally in the upper part of a container plate (92) whose position is in turn above the On/Off air solenoid valve arrangement (40) and the oxygen On/Off solenoid valve (60) so that the heat generated by the latter is transferred to the humidifier (90) and its contents, generating an increase in the water temperature that allows raising the temperature of the water in the interior of the humidifier (90) and in this way provide the air/oxygen mixture with humidity and also an increase in temperature, since it has an upward path through the humidifier (90) every time a connector is inserted inside (95) that rec It runs all its height and where, in turn, it has a mixing outlet (93) arranged in an area close to the upper part of said humidifier (90), which is connected by means of a connector (94) that guides the mixture at a height close to the top of the humidifier (90) to be sensed by a flow sensor (100) that is responsible for controlling and monitoring the programmed number of liters of air per minute of the requirements of the patient's condition and that also communicates a signal to the microcontroller to modify the flow of gases through the pressure control solenoid valve (70). Consequently, the flow sensor (100) is connected to a means of driving the air/oxygen mixture (105) that has a downward orientation that finally leads the mixture towards an air/oxygen outlet (110) arranged in the middle zone, between the fluid inlet conductors and the flow sensor, and arranged vertically with respect to an outlet (111) arranged perpendicular to the axial axis of the air/oxygen outlet (110) directed towards the patient during the inspiration process.

When the air/oxygen mixture ends its stay inside the body of a patient and gives way to the fluid coming out of the patient, manifesting the presence of CO2, said fluid coming from the lungs that operates in the expiration process, is channeled to a CO2 outlet (115) that is located in the lower part of the air/oxygen outlet (110), and which is interconnected with a CO2 outlet solenoid valve (120) that finally leads to this gas, through from a gas outlet tube (125), to a PEEP valve (140), where the latter maintains, by releasing CO2 into the atmosphere, a positive pressure in the respiratory arrangement and therefore, a remaining volume at end of expiration, with the aim of maintaining an opening in the alveoli in order to reduce the risk of generating some lung damage due to their collapse. This PEEP valve (140) is controlled by a servomotor (141) which in turn is controlled by the microcontroller. In one embodiment of the present invention, the servo motor (141) can be replaced by a stepper motor.

In addition, there is a differential pressure sensor (130) interconnected at one end to a primary differential pressure conductor (131) which, in turn, is coupled to a through bore (111) that is located at the air outlet./oxygen (110), and at its opposite end to a secondary differential pressure conductor (132) that is arranged in the gas outlet tube (125), at the inlet of the PEEP valve (140), where this sensor of differential pressure (130), several times per second, checks the inspiration and expiration and inlet/outlet gas pressures so that, if necessary, by means of the solenoid valve Pressure control (70), the pressures are increased or decreased to maintain the programmed levels and required by the patient's condition.

In a preferential embodiment, the gas outlet tube (125) internally has an air quality sensor to monitor CO2 on expiration.

The process of managing the gas mixture and conduction towards a user, is given by the microcontroller that controls the opening and closing of the Air On/Off solenoid valve (40) and the Oxygen On/Off solenoid valve (60). through a double action relay (not shown), as well as controlling the $CO_2$ output solenoid valve (120) that controls the expiration output, which is also controlled by this same relay, as follows:

When the microcontroller determines the closure of the CO2 outlet solenoid valve (120), it opens the air on/Off solenoid valve (40) and the oxygen on/Off solenoid valve (60) to allow a previously programmed amount of oxygen to pass to the patient. air/oxygen, in this way, closing the CO2 outlet solenoid valve (120) prevents loss of pressure through the outlet, thus ensuring that the air/oxygen mixture directed to the patient can only exit through the air/oxygen outlet (110) into the lungs.

Upon reaching the point of expiration, the microcontroller closes the arrangement of the air On/Off solenoid valve (40) and the oxygen On/Off solenoid valve (60), and opens the CO2 output solenoid valve (120), allowing the air to expired leaves through the $CO_2$ outlet (115) and cannot be diverted or returned through the air/oxygen mixture conduction means (105).

Figure 9:
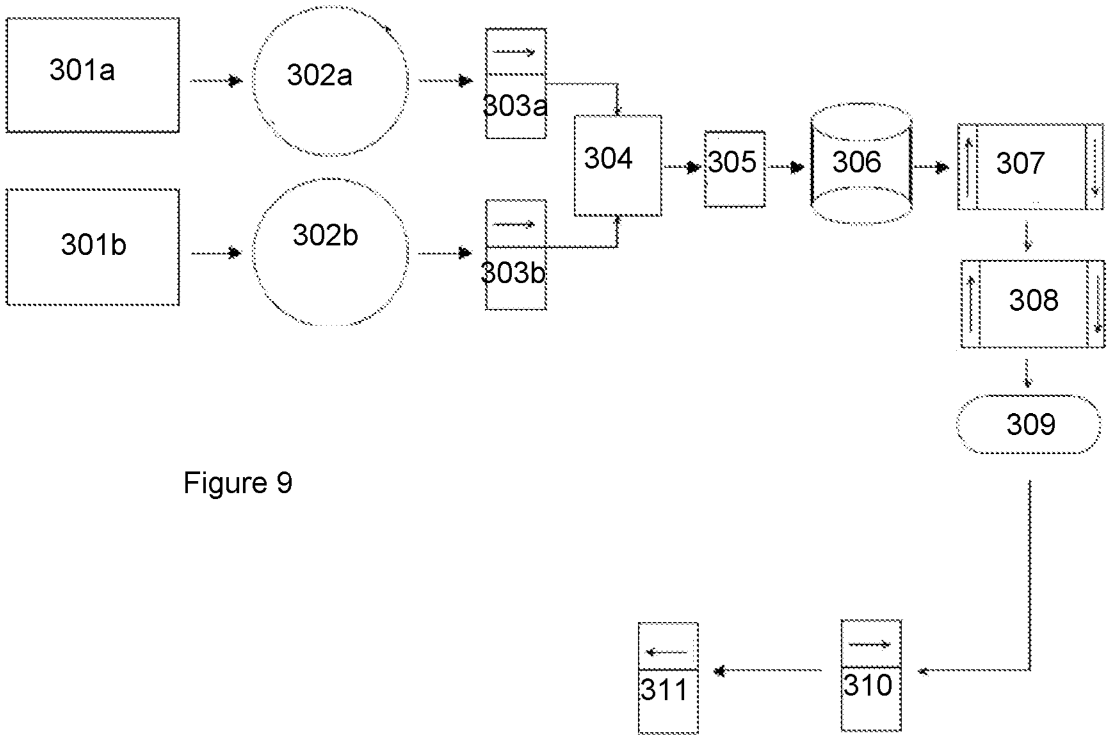
FIG. 9 shows a block diagram related to the respiratory support method of the invention.

According to FIG. 9, the respiratory support method (300) comprising the steps of: receiving a flow of oxygen (301*a*) through from an oxygen source through an oxygen inlet nozzle; receiving a flow of air (301*b*) from a source of compressed air through an air inlet; regulating the flow of oxygen (302*a*) by means of an oxygen pressure regulator; regulating the air flow (302*b*) by means of an air pressure regulator; control the passage of the regulated oxygen flow (303*a*) by means of an oxygen On/Off solenoid valve; control the passage of the regulated air flow (303*b*) by means of an air On/Off solenoid valve; presetting (304) through a plurality of graphical user interfaces displayed by a user interface, the values related to the tidal volume, positive end-expiratory pressure, trigger pressure, fraction of inspired oxygen, the respiratory rate, and the inspiration/expiration ratio according to the patient's needs; mix (305) the oxygen and air provided by the oxygen and air On/Off solenoid valves; humidifying and increasing the temperature (306) of the moisture air/oxygen mixture by means of a humidifier; sensing (307) the value related to the amount of liters of air per minute (volume) of the wet mix by means of a flow sensor; sensing (308) the value related to the pressure of the inspiration and expiration gases through the inlet/outlet differential pressure sensor; leading (309) the moistened mixture at a previously determined pressure and volume towards an air/oxygen outlet channel that leads towards a patient during the inspiration process; monitoring (310) the value of CO2 contained in the exhaled gases by means of an exhaled air quality sensor to establish; regulate (311) automatically and in real time the oxygen pressure supplied to the patient as well as the number of liters of air per minute (volume) of the wet mixture;

It should be noted that, under normal conditions, the programmed values should be absolute and constant to keep the patient's breathing in optimal conditions. However, in practice this is not the case, since the patient's conditions are by no means stable and due to these variations, the programmed values become relative and variable as well.

For this reason, the microprocessor is programmed with control algorithms which a person with expertise in the matter can understand that are not typical of a computer program that runs any conventional computer. Said algorithms were specially designed for the operation of the apparatus of the present invention, to modify in real time said values, which without complicated equations, only decide to increase or decrease the pressures, flow and times based on the differences between what is programmed and what is expected, which is sensed in each respiratory cycle, and in this way, the microprocessor will send the corrections to the solenoid valves, in order to compensate the differences that could arise between the programmed values and the real values necessary.

Thus, the microprocessor through the sensed parameters (approximately 1000 times per second) by the differential pressure and flow sensors, in each respiratory cycle it performs the steps of: control, by means of the air and oxygen solenoid valves, the flow and pressure of air and oxygen supplied to the patient in each respiratory cycle at starting from the preset values related to inspiration, plateau and expiration, as well as the positive pressure at the end of expiration; process the sensed values related to the pressure of the inspiration and expiration gases to determine in real time from said result the real value of the pressure of the wet mixture supplied to the patient; processing the sensed values related to the volume of the wet mix to determine in real time the amount of volume of the wet mix delivered to the patient; process the sensed values related to the pressure of the inspiration and expiration gases, and determine in real time from said result the real value of the pressure of the humid mixture; process and determine the values related to the CO2 contained in the exhaled gases to define the opening and closing of a CO2 outlet solenoid valve that releases the gases produced by the patient's exhalation, determine in real time that the preset values correspond to the sensed values, which must be absolute and constant to keep the patient's breathing in optimal conditions; send in real time at least one control signal to the oxygen and/or air On/Off solenoid valves in order to compensate at least one difference in pressure between what is programmed and what is sensed in each respiratory cycle; send at least one control signal to the pressure control solenoid valve in real time in order to compensate for at least a difference between the programmed number of liters of air per minute according to the requirements of the patient's condition and what is sensed at each respiratory cycle; send in real time at least one control signal to the CO2 outlet solenoid valve in the event that the value of the remaining volume at the end of expiration sensed is less than the preset value.

In this way, when the patient reaches a point of inspiration, the microprocessor closes the CO2 outlet solenoid valve, opens the air on/Off solenoid valve and the oxygen On/Off solenoid valve, allowing a previously programmed amount to pass to the patient. of air/oxygen, avoiding the loss of pressure through the outlet, thus guaranteeing that the air/oxygen mixture directed to the patient can only exit through the air/oxygen outlet towards the lungs.

Likewise, when the patient reaches an expiration point, the microprocessor closes the arrangement of the air On/Off solenoid valve and the oxygen On/Off solenoid valve and opens the CO2 outlet solenoid valve, with the exhaled air leaving through the $CO_2$ outlet and cannot be diverted or returned by the air/oxygen mixture conduction medium.

Additionally, and in a second embodiment of the invention, there is an oximeter that measures oxygen saturation and heart rate, so the vital signs monitored are:

Breathing frequency

Heart rate

Figure 18:
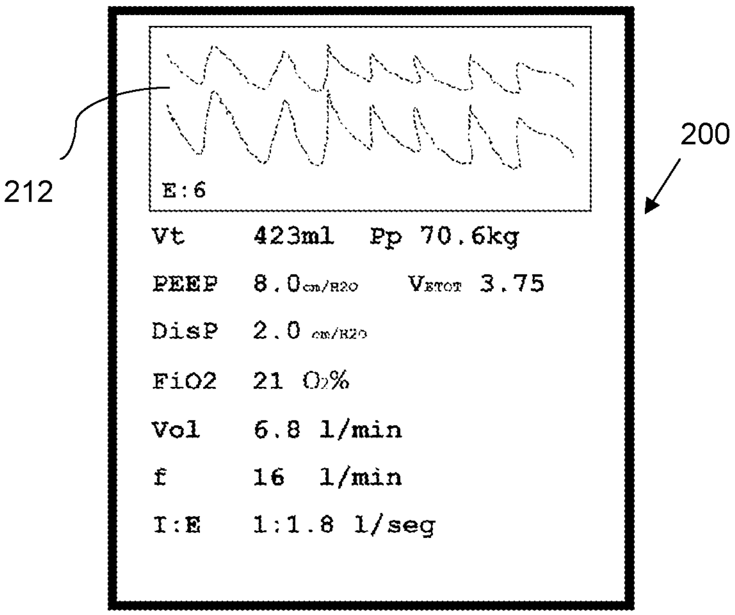
FIG. 18 shows an example of the respiratory support device screen to display the programmed values.

Oxygen saturation in the blood.

Where these are also shown preferentially in the graphical user interface of the screen in FIG. 18.

The sequence in the microcontroller is arranged to provide a constant flow of air/oxygen mixture, and to be able to control the solenoid valves of the arrangement, for which only the gender and weight of the patient expressed in kilograms is required, so the steps executed by the microcontroller are the following:

measure patient

Calculate predicted weight=(cm-152.4)0.9+G

G=50 MEN

G=45.5 WOMEN

PROGRAM FAN

VOL TIDAL—6 ml X (predicted weight) PEEP SaO2/FiO2

If the PEEP is GREATER than 190. PEEP=5 to 8 mmH20

If the PEEP is LESS than 190 PEEP=10 mmH20

FiO2—SaO2 from 88 to 94%

Trigger—2 cmH20 L/min

RF 16 A at 20 X minute—PaCO2 normal (35-45)(<60 mmHg)

I:E Adjust Flow: Ti-1:2.

Figure 10:
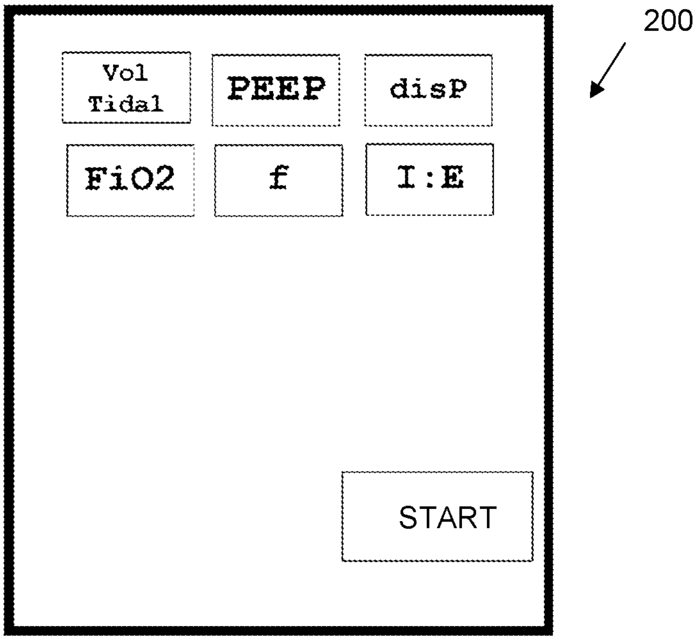
FIG. 10 shows an example of the respiratory support device screen in start menu mode.

Therefore, as shown in FIG. 10, there is a user interface (200) which, according to the preferred embodiment of the invention, consists of a touch screen (not limited to it) that displays a first graphical interface where the parameters to be monitored within the device are displayed, Tidal Volume, Positive End Expiratory Pressure (PEEP), trigger pressure (disp), fraction of inspired oxygen (Fio2), respiratory rate (f), and inspiration/expiration (I:E) ratio, as well as a start button.

Figure 11:
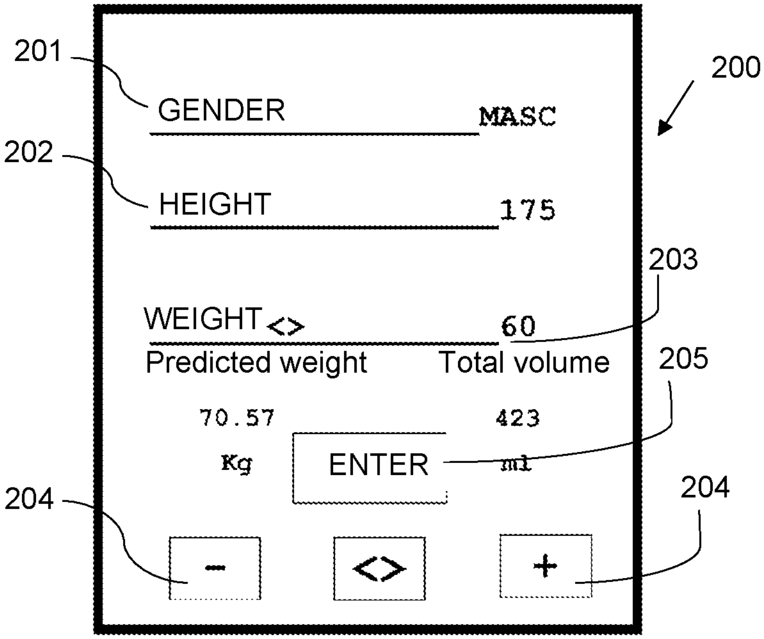
FIG. 11 shows an example of the ventilator screen during Tidal Volume programming.
Figure 12:
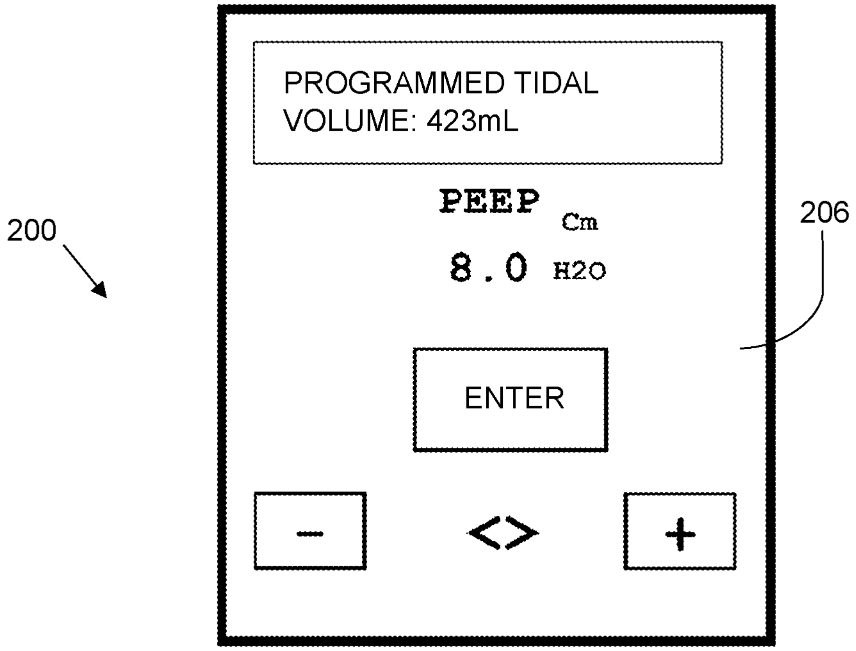
FIG. 12 shows an example of the respiratory support screen during positive end-expiratory pressure programming.
Figure 13:
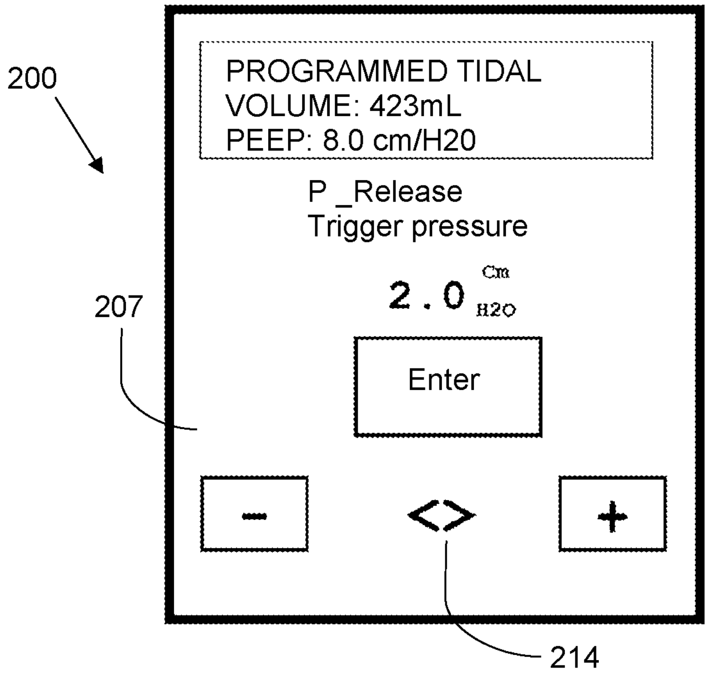
FIG. 13 shows an example of the screen of the respiratory assistance device in the programming of the shot by pressure or trigger.
Figure 14:
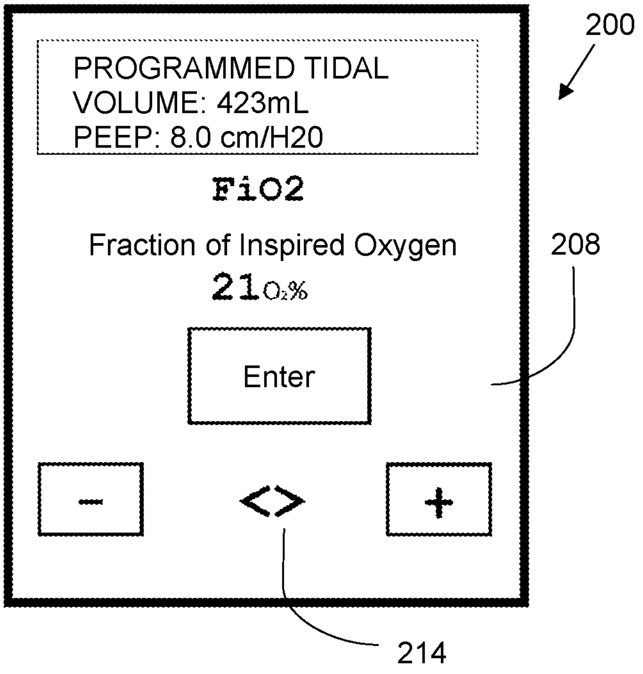
FIG. 14 shows an example of the screen of the respiratory support device in the programming of the fraction of inspired oxygen.
Figure 15:
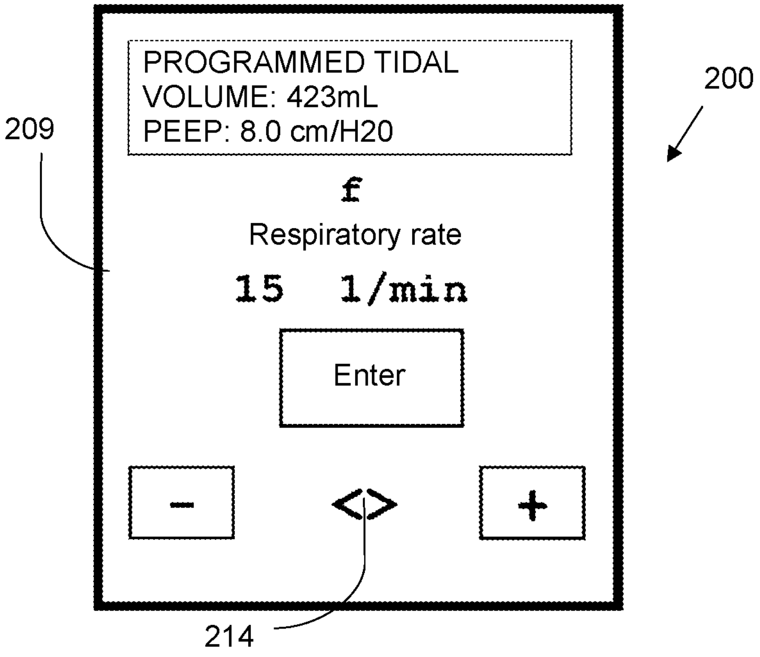
FIG. 15 shows an example of the ventilator screen in respiratory rate programming.
Figure 16:
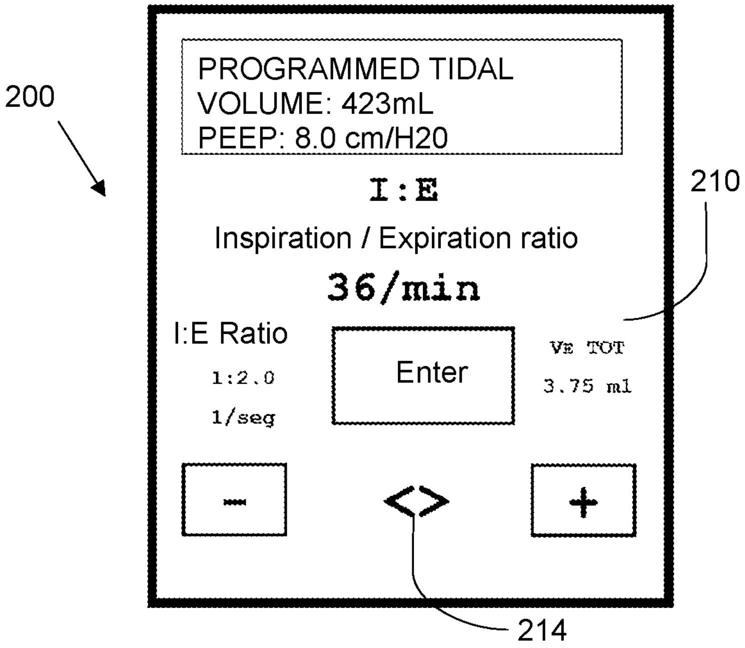
FIG. 16 shows an example of the screen of the respiratory assistance device in the programming of the inspiration/expiration ratio.

Subsequently, according to FIG. 11, there is a second graphic interface that displays the user interface (200) where the data related to: gender (201)(MASLE OR FEMALE), height (202) expressed in centimeters and the weight (203) expressed in kilograms where the input of the information can be adjusted by means of two buttons (204) to increase or decrease the flow generation parameters; when these parameters have been entered the enter button (205) is pressed.

Likewise, FIGS. 12 to 16 show other graphical interfaces displayed by the user interface (200) that eventually display the data of Tidal Volume, Positive end-expiratory pressure (PEEP) (206), pressure trigger (disp)(207), fraction of inspired oxygen (Fio2)(208), respiratory rate (f) (209), and inspiration/expiration ratio (I:E)(210).

Figure 17:
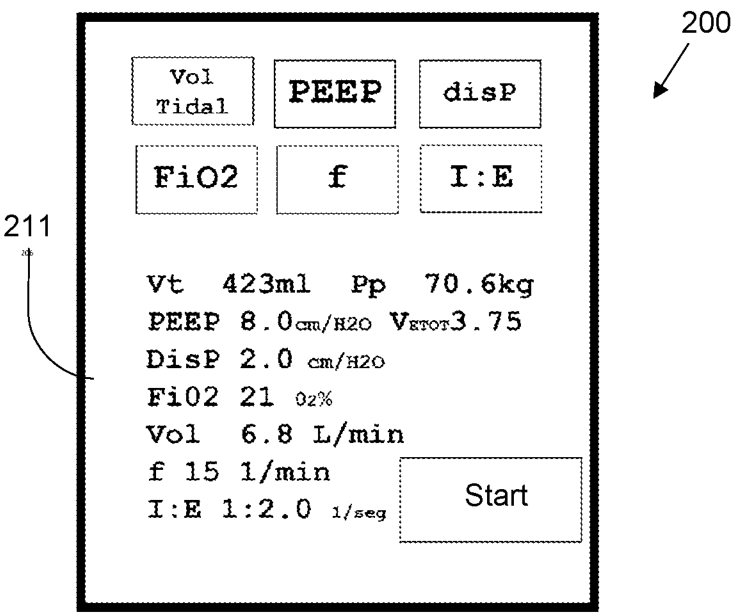
FIG. 17 shows an example of the respiratory support device screen.

Finally, as shown in FIG. 17, the data is compiled on a screen for final review (211) and the generation of a graph (212) that is displayed to show the patient's respiratory rate, as shown in FIG. 17.

For the selection of the parameters in each of the interfaces, there are some selection buttons (214) located at the bottom of each of the interfaces and that allow a variation in the selection of the selected parameter. These buttons selection are disabled when their use is not required.

In a third additional embodiment of the invention, an additional circuit is included to provide storage, where it is connected in a wired or wireless manner, to a network, by means of which it provides information to be stored in the cloud, where it is integrated by a data storage and distribution unit to transfer this data in order to deposit it in an integrated storage, including local storage and cloud storage; It also has a storage management unit that connects with the integrated storage in order to arrange the data and provide information on the parameters monitored in the respiratory support device, where the storage levels are related to the amount of data stored; it also has a data handling unit to provide integrated storage as virtual data storage regardless of the location in which the data is stored and a storage connection unit to provide a user interface for data storage virtual as a single virtual storage unit; furthermore this data handling unit provides a write buffer function or a read cache function for the data and decreases the response time of a write operation or a read operation for the data using high-speed storage.

Considering that the above scheme is developed by a method for providing storage for providing a cloud service, performed by an apparatus for providing storage for providing a cloud service, which is integrated by a data distributor to store data in integrated storage, including local storage and cloud storage; and manage data by providing embedded storage as virtual data storage, regardless of the cloud location of this data.

In a fourth embodiment of the invention there is included an alarm detection device configured to compare physiological data received through the patient monitoring unit, wherein the alarm detection device responds to a pre-defined measurement of physiological data as They are hypertension or hypotension, heart rhythm outside the parameter, hypoxia, hyperventilation, where in turn, an alarm detection device is configured to initiate an alarm that comprises at least one speaker with a first frequency, waveform or duty cycle configured to output a first alarm signal and a second alarm signal having a second frequency, waveform, or duty cycle different from the first frequency, for wave ma or duty cycle, there is also an alarm device that emits the second signal if the first signal is emitted and the alarm confirmation mechanism is not activated before the specified event, where the alarm device is configured to gradually increase the second frequency of the second alarm signal until the second frequency reaches a peak frequency or a confirmation notification mechanism is activated.

There is also a notification device in case of electrical failure, where in addition to activating a backup battery, it includes an acoustic sensor configured to generate a sensor signal in response to an acoustic alarm indicative of electrical failure, a unit signal processing in communication with the acoustic sensor and configured to generate an identification signal when the sensor signal of the acoustic sensor satisfies an identification criterion.

Having that the alarm system is connected to an interface unit in communication with the signal processing unit and configured to produce and send a message signal to a medical center call system, in response to the processing identification signal.

Although a preferred exemplary embodiment is shown and specified in detail in the drawings and the specification above, these are to be viewed as purely exemplary and not as limiting of the invention. In this regard, it is noted that only the preferred exemplary embodiment is shown and specified, and all variations and modifications are to be presently or future protected within the scope of protection of the invention as defined in the claims.

REFERENCE LIST

1 Respiratory support device
5 Inlet section
6 Air compressor
7 Oxygen tank
8 Air connector
9 Second oxygen inlet channel
10 Primary Channel
11 Connector
12 Oxygen connector
13 Oxygen inlet nozzle
15 Connections to air/oxygen supplies
16 Air/oxygen outlet
17 Face mask
20 Pressure regulator
21 Manometer
30 First tube initial air
40 On/off solenoid valve
41 On/off solenoid valve connection
50 Initial oxygen tube
60 Oxygen on/off solenoid valve
61 Connection with oxygen on/off valve
65 Air/oxygen outlet
70 Pressure control solenoid valve
80 Stepper motor or servo motor
90 Humidifier
91 Connection Means
92 Container plate
93 Mix outlet
95 Connector
100 Flow sensor
105 Conduction medium for the air/oxygen mixture
110 Air/oxygen outlet
111 Exit
115 CO2 output
120 CO2 outlet solenoid valve
125 Exhaust pipe
130 Differential Pressure sensor
131 Differential pressure primary driver
132 Secondary conductor differential depression
140 PEEP valve
141 Stepper motor
201 Gender
202 Stature
203 Weight
204 Buttons
205 Enter
206 Positive End Expiratory Pressure (PEEP)
207 Pressure release (trip)
208 Fraction of inspired oxygen (Fio2)
209 Respiratory rate (f)
210 Inspiration/expiration ratio (I:E)
211 Final review
212 Graphic
214 Radio buttons

The invention claimed is:

1. A respiratory assistance device (1) comprising:

an inlet (10) including a cylindrical conductor interconnected with an arrangement made up of a connector (11), a pressure regulator (20), a manometer (21), an initial air tube (30) and an air on/off air solenoid valve (40);

an oxygen inlet nozzle (13) including an initial oxygen tube (50), which has a rib at each of two opposite ends, and an oxygen on/off solenoid valve (60);

a pressure control solenoid valve (70) connected to a humidifier (90) by means of a connection channel (91);

an air/oxygen outlet (110) interconnected to a mix conduction means (105) which is in turn interconnected with a flow sensor (100), and with a mix outlet (93) of the humidifier (90) by means of a connector (94); and a $CO_2$ outlet means (115) interconnected with a CO2 outlet solenoid valve (120) which is interconnected with a gas outlet tube (125) and with a PEEP valve (140);

a microcontroller configured to executes the following steps based on parameters sensed by the flow sensor (100) and a differential pressure sensor (130), during each respiratory cycle:

controlling, by the air and the oxygen solenoid valves, the flow and pressure of air and oxygen supplied to the patient in each respiratory cycle from pre-established values related to inspiration, plateau and expiration, as well as the positive pressure at the end of the expiration;

processing sensed values related to the pressure of the inspiration and expiration gases to determine in real time from said result a real value of the pressure of a wet mixture supplied to the patient;

processing sensed values related to a volume of the wet mix to determine in real time an amount of the volume of the wet mix delivered to the patient;

processing the sensed values related to the pressure of the inspiratory and expiratory gases to determine in real time from said result an actual value of the pressure of the wet mix;

processing and determining values related to the $CO_2$ contained in the exhaled gases to define an opening and a closing of the $CO_2$ outlet solenoid valve that outlets the gases produced by the patient's expiration by using an exhale air quality sensor, determining in real time that preset values correspond to the sensed values, which must be absolute and constant to maintain the patient's breathing in optimal conditions;

sending in real time at least one control signal to the oxygen and/or the air on/off solenoid valves in order to compensate at least one difference in pressure between the preset values and the sensed values in each respiratory cycle;

sending at least one control signal to the pressure control solenoid valve in real time in order to compensate for at least a difference between a preset volume according to the requirements of patient's condition and the sensed values at each respiratory cycle;

sending in real time at least one control signal to the $CO_2$ outlet solenoid valve in an event that a value of a remaining volume at the end of expiration sensed is less than the preset value.

2. The respiratory assistance device (1) according to claim 1, wherein both the air on/off solenoid valve (40) and the oxygen on/off solenoid valve (60) are coupled together.

3. The respiratory assistance device (1) according to claim 1, further comprising: an air/oxygen outlet (65) interconnected to the pressure control solenoid valve (70), wherein the pressure control solenoid valve is controlled by a servomotor (80).

4. The respiratory assistance device (1) according to claim 1, wherein the humidifier (90) is made up of a cylinder container and is arranged centrally in an upper part of a container plate (92), which is positioned above the arrangement of the air on/off solenoid valve (40) and the oxygen on/off solenoid valve (60) in order to heat a humidified air.

5. The respiratory assistance device (1) according to claim 1, wherein the differential pressure sensor (130) is coupled by a differential pressure conduit (131) to a hole (111) in the air/oxygen outlet (110) and by a secondary conductor (132) to the gas outlet tube (125).

6. The respiratory assistance device (1) according to claim 1, further comprising a servomotor and/or stepper motor (141) to control the PEEP valve (140).

7. The respiratory assistance device (1) according to claim 6, wherein the servomotor and/or stepper motor (141) is controlled by the microcontroller.

8. The respiratory assistance device (1) according to claim 1, wherein the gas outlet tube (125) internally carries an air quality sensor.

9. The respiratory assistance device (1) according to claim 1, further comprising a system configured to collect, and process data, and transfer data to a wired or wireless manner.

10. The respiratory assistance device (1) according to claim 1, further comprising a first air connector (8) and a second oxygen connector (12) arranged in parallel and horizontally.

11. The respiratory assistance device (1) according to claim 1, further comprising a hexagonal-shaped connector (11) between the initial air tube (30) and the air on/off solenoid valve (40).

12. The respiratory assistance device (1) according to claim 11, wherein the pressure control solenoid valve (70) is controlled by a stepper motor.

13. The respiratory assistance device (1) according to claim 1, further comprising a hexagonal-shaped connector (61) between the initial oxygen tube (50) and the oxygen on/off solenoid valve (60).

14. The respiratory assistance device (1) according to claim 1, further comprising a computer arrangement configured to collect and transmit data to a cloud.

15. The respiratory assistance device (1) according to claim 1, further comprising an alarm system in case of confirmation of a parameter out of range.

16. The respiratory assistance device (1) according to claim 1, further comprising a normal air channel (**8*a*), wherein the normal air channel (8*a*) and the oxygen channel (9) are fed by air/oxygen supplies (15**) which are part of medical units.

17. The respiratory assistance device (1) according to claim 1, further comprising a pressure regulator and a manometer at the oxygen inlet (13).

18. A method of respiratory assistance comprising the steps of:

controlling a passage of an oxygen flow regulated by using an oxygen on/off solenoid valve;

controlling a passage of a regulated air flow by using an air on/off solenoid valve;

receiving preset values related to tidal volume, positive end-expiratory pressure, trigger pressure, fraction of inspired oxygen, respiratory rate, and inspiration ratio/expiration through a plurality of graphical user interfaces displayed by a user interface according to a patient's needs;

mixing the oxygen flow and the regulated air provided by the oxygen and air on/off solenoid valves;

humidifying and increasing a temperature of a wet mix by using a humidifier;

sensing a value related to a volume of the wet mix by a flow sensor;

sensing a pressure of the inspiration and expiration gases through a differential pressure sensor;

conducting the wet mix at a previously established pressure and volume towards an air/oxygen outlet channel that leads towards the patient during an inspiration process;

monitoring a value of $CO_2$ contained in exhaled gases by an exhaled air quality sensor;

regulating automatically and in real time through a microcontroller an oxygen pressure supplied to the patient, as well as the volume of the wet mixture;

where a method of regulation of the oxygen and the volume of the wet mix comprises the steps of:

controlling using the air and oxygen solenoid valves, the flow and the pressure of air and oxygen supplied to the patient in each respiratory cycle from pre-established values related to inspiration, plateau and expiration, as well as a positive pressure at an end of the expiration;

processing sensed values related to a pressure of an inspiratory gas and an expiratory gases to determine in real time from a result a real value of the pressure of the wet mix supplied to the patient;

processing sensed values related to the volume of the wet mix to determine in real time an amount of the volume of the wet mix delivered to the patient;

processing the sensed values related to the pressure of the inspiratory gas and the expiratory gas, determining in real time from a result an actual value of the pressure of the wet mix;

processing and determining values related to the $CO_2$ contained in the exhaled gases to define an opening and closing of a $CO_2$ outlet solenoid valve that outlets the gases produced by the patient's expiration, determining in real time that the preset values correspond to the sensed values, which must be absolute and constant to maintain the patient's breathing in optimal conditions;

sending in real time at least one control signal to the oxygen and/or air on/off solenoid valves in order to compensate at least one difference in pressure between the preset values and the sensed values in each respiratory cycle;

sending the at least one control signal to the pressure control solenoid valve in real time in order to compensate for at least a difference between a preset volume according to requirements of the patient's condition and the sensed values; and sending in real time the at least one control signal to the CO2 outlet solenoid valve in an event that a value of a remaining volume at the end of expiration sensed is less than the preset value.

19. The method of respiratory assistance according to claim 18, wherein when the patient reaches an inspiration point, the microprocessor closes the $CO_2$ outlet solenoid valve, opens the oxygen on/off solenoid valve and the air on/off solenoid valve, allowing a previously programmed amount of air/oxygen to pass to the patient, avoiding pressure loss through the air/oxygen outlet, thus guaranteeing that the air/oxygen mixture directed at the patient can only exit through the air/oxygen outlet towards the patient's lungs.

20. The method of respiratory assistance according to claim 18, wherein when the patient reaches an expiration point, the microprocessor closes the air on/off solenoid valve and the oxygen on/off solenoid valve and opens the CO2 outlet solenoid valve, with the exhaled gases leaving through the $CO_2$ outlet and cannot be diverted or returned through an air/oxygen mixture conduction device.

* * * * *